(12) United States Patent
Lallemand et al.

(10) Patent No.: US 9,089,480 B2
(45) Date of Patent: Jul. 28, 2015

(54) ANIONIC OIL-IN-WATER EMULSIONS CONTAINING PROSTAGLANDINS AND USES THEREOF

(75) Inventors: Frederic Lallemand, Fresnes (FR); Betty Phillips, Antony (FR); Jean-Sebastien Garrigue, Verrieres le Buisson (FR)

(73) Assignee: SANTEN SAS, Evry (FR)

( * ) Notice: Subject to any disclaimer, the term of this patent is extended or adjusted under 35 U.S.C. 154(b) by 0 days.

(21) Appl. No.: 13/203,756

(22) PCT Filed: Mar. 4, 2010

(86) PCT No.: PCT/EP2010/052740
§ 371 (c)(1),
(2), (4) Date: Aug. 29, 2011

(87) PCT Pub. No.: WO2010/100217
PCT Pub. Date: Sep. 10, 2010

(65) Prior Publication Data
US 2011/0319488 A1    Dec. 29, 2011

Related U.S. Application Data

(60) Provisional application No. 61/157,347, filed on Mar. 4, 2009.

(30) Foreign Application Priority Data

Mar. 4, 2009    (EP) .................................... 09305203

(51) Int. Cl.
| A61K 31/5575 | (2006.01) |
| A61K 9/00 | (2006.01) |
| A61K 47/10 | (2006.01) |
| A61K 47/26 | (2006.01) |
| A61K 47/44 | (2006.01) |

(52) U.S. Cl.
CPC ........... *A61K 9/0048* (2013.01); *A61K 31/5575* (2013.01); *A61K 47/10* (2013.01); *A61K 47/26* (2013.01); *A61K 47/44* (2013.01)

(58) Field of Classification Search
CPC .................................................. A61K 31/5575
USPC ....................................................... 514/530
See application file for complete search history.

(56) References Cited

U.S. PATENT DOCUMENTS

| 4,599,353 A | 7/1986 | Bito |
| 4,684,633 A | 8/1987 | Imagawa et al. |
| 5,588,559 A | 12/1996 | Vallet Mas et al. |
| 5,688,819 A | 11/1997 | Woodward et al. |
| 5,849,792 A | 12/1998 | Schneider |
| 6,007,826 A | 12/1999 | Benita et al. |
| 6,011,062 A | 1/2000 | Schneider et al. |
| 6,342,524 B1 | 1/2002 | Hellberg et al. |
| 7,064,109 B2 | 6/2006 | Luyckx et al. |
| 8,697,751 B2 | 4/2014 | Sakai et al. |
| 2004/0082660 A1 | 4/2004 | Ueno |
| 2004/0115234 A1 | 6/2004 | Gewirtz |
| 2004/0198829 A1 | 10/2004 | Sponsel et al. |
| 2005/0124699 A1 | 6/2005 | Akiba et al. |
| 2008/0268020 A1 | 10/2008 | Philips et al. |
| 2009/0298956 A1 | 12/2009 | Chowhan et al. |
| 2011/0118349 A1 | 5/2011 | Garrigue et al. |
| 2011/0313038 A1 | 12/2011 | Lallemand et al. |
| 2012/0225939 A1 | 9/2012 | Garrigue et al. |

FOREIGN PATENT DOCUMENTS

| CN | 101282714 A | 10/2008 |
| CN | 101516332 A | 8/2009 |
| CN | 102341094 A | 2/2012 |
| EP | 0423697 A2 | 4/1991 |
| EP | 0696452 A1 | 2/1996 |
| EP | 1532981 A1 | 5/2005 |
| EP | 1547599 A1 | 6/2005 |
| EP | 1655021 A1 | 5/2006 |
| EP | 1 681 059 A1 | 7/2006 |
| EP | 1 972 334 A1 | 9/2008 |
| EP | 1 985 298 A1 | 10/2008 |
| EP | 1985298 A1 * | 10/2008 |
| EP | 1994933 A1 | 11/2008 |
| EP | 2127638 A1 | 12/2009 |
| JP | 7-504848 A | 6/1995 |
| KR | 20030046553 A | 6/2003 |
| MX | 2010012987 A | 2/2011 |
| WO | 9318852 A1 | 9/1993 |
| WO | 03053405 A1 | 7/2003 |
| WO | 2005044276 A1 | 5/2005 |
| WO | 2006050836 A2 | 5/2006 |
| WO | 2007/042262 A2 | 4/2007 |
| WO | 2007042262 A2 | 4/2007 |
| WO | WO 2007042262 A2 * | 4/2007 |
| WO | 2007089931 A1 | 8/2007 |

(Continued)

OTHER PUBLICATIONS

Laura Rabinovich-Guilatt, Patrick Couvreur, Gregory Lambert, Danny Goldstein, Simon Benita, Catherine Dubernet, Extensive surface studies help to analyse zeta potential data: the case of cationic emulsions, Chemistry and Physics of Lipids 131 (2004) 1-13.*

(Continued)

*Primary Examiner* — Kendra D Carter
*Assistant Examiner* — Jason A Deck
(74) *Attorney, Agent, or Firm* — Young & Thompson

(57) ABSTRACT

A colloidal anionic oil-in-water emulsion includes a prostaglandin, an oil having a iodine value ≤2, a surfactant and water, provided the anionic oil-in-water emulsion does not contain polyvinyl alcohol. The use of the anionic oil-in-water emulsions for enhancing the stability of the prostaglandins, for the treatment of ocular hypertension and/or glaucoma, for promoting growth of eyelashes and/or for treating eyelash hypotrichosis is also described.

15 Claims, 1 Drawing Sheet

(56) References Cited

FOREIGN PATENT DOCUMENTS

| WO | 2008012367 A2 | 1/2008 |
|---|---|---|
| WO | 2008036847 A2 | 3/2008 |
| WO | 2008074885 A2 | 6/2008 |
| WO | 2009145356 A1 | 12/2009 |
| WO | 2010100218 A1 | 9/2010 |

OTHER PUBLICATIONS

International Search Report, dated Aug. 20, 2010, from corresponding PCT application.
Baudouin et al., "In Vitro Studies of Antiglaucomatous Prostaglandin Analogues: Travoprost with and without Benzalkonium Chloride and Preserved Latanoprost", Investigative Ophthalmology & Visual Science, 2007, vol. 48, No. 9, pp. 4123-4128.
Choi et al., "Low toxicity of cationic lipid-based emulsion for gene transfer", Biomaterials, 2004, pp. 5893-5903, vol. 25.
Chung et al., "CREB Mediates Prostaglandin F2α-Induced MUC5AC Overexpression", J. Immunol., 2009, vol. 182, No. 4, pp. 2349-2356.
Database WPI, Section Ch, Week 200377, Derwent Publications Ltd., London, GB; Class A96, AN 2003-826210, XP002397839 & KR2003046553A, 2003.
Debbasch et al., "Quaternary Ammoniums and Other Preservatives' Contribution in Oxidative Stress and Apoptosis on Chang Conjunctival Cells", Investigative Ophthalmology & Visual Science, Mar. 2001, pp. 642-652, vol. 42, No. 3, Association for Research in Vision and Ophthalmology.
Dilly et al., "Surface changes in the anaesthetic conjunctiva in man, with special reference to the production of mucus from a non-goblet-cell source", British Journal of Ophthalmology, 1981, vol. 65, pp. 833-842.
Erb et al., "German register for glaucoma patients with dry eye. I. Basic outcome with respect to dry eye", Graefes Arch Clin. Exp. Ophthalmol., 2008, vol. 246, pp. 1593-1601.
Furrer et al., "Ocular tolerance of preservatives and alternatives", European Journal of Pharmaceutics and Biopharmaceutics, 2002, pp. 263-280, vol. 53.
Greiner et al., "Mucus Secretory Vesicles in Conjunctival Epithelial Cells of Wearers of Contact Lenses", Arch Ophthalmol., 1980, vol. 98, pp. 1843-1846.
Gronert, Karsten, "Lipid Autacoids in Inflammation and Injury Responses, A Matter of Privilege", Molecular Interventions, 2008, vol. 8, No. 1, pp. 29-35.
Han et al., "Partition of antimicrobial additives in an intravenous emulsion and their effect on emulsion physical stability", Int. J. Pharm., 2005, pp. 263-271, vol. 288.
Jumaa et al., "Physicochemical properties of chitosan-lipid emulsions and their stability during the autoclaving process", International Journal of Pharmaceutics, 1999, pp. 175-184, vol. 183.
Jumaa et al., "A new lipid emulsion formulation with high antimicrobial efficacy using chitosan", European Journal of Pharmaceuticals and Biopharmaceuticals, 2002, pp. 115-123, vol. 53.
Klang et al., "The stability of piroxicam incorporated in a positively-charged submicron emulsion for ocular administration", International Journal of Pharmaceutics, 1996, pp. 33-44, vol. 132.
Klang, et al., "Physicochemical characterization and acute toxicity evaluation of a positively-charged submicron emulsion vehicle", J. Pharm. Pharmacol., 1994, pp. 986-993, vol. 46, abstract.
Klang et al., "Influence of emulsion droplet surface charge on indomethacin ocular tissue distribution", Pharm. Dev. Technol., 2000, pp. 521-532, vol. 5, abstract.
Klang et al., "Evaluation of a positively charged submicron emulsion of piroxicam on the rabbit corneum healing process following alkali burn", Journal of Controlled Release, 1999, vol. 57, pp. 19-27.
Landreville et al., "Expression of Phospholipases A2 and C in Human Corneal Epithelial Cells", Investigative Ophthalmology & Visual Science, 2004, vol. 45, No. 11, pp. 3997-4003.
Leung et al., "Prevalence of Ocular Surface Disease in Glaucoma Patients", J. Glaucoma, 2008, vol. 17, No. 5, pp. 350-355.
Liu et al., "New cationic lipid formulations for gene transfer", Pharm Res., 1996, vol. 13, No. 12, pp. 1856-1860, abstract.
McCarey et al., "In Vivo Corneal Epithelial Permeability following Treatment with Prostaglandin Analoges with or without Benzalkonium Chloride", Journal of Ocular Pharmacology and Therapeutics, 2007, vol. 23, No. 5, pp. 445-451.
Mietz et al., "Latanoprost Stimulates Secretion of Matrix Metalloproteinases in Tenon Fribroblasts Both In Vitro and In Vivo", http://www.iovs.org/content/44/12/5182.long, Feb. 15, 2011.
Ogawa et al., "Production and Characterization of O/W Emulsions Containing Cationic Droplets Stabilized by Lecithin-Chitosan Membranes", Journal of Agricultural and Food Chemistry, 2003, vol. 51, pp. 2806-2812.
Ott et al., "A cationic sub-micron emulsion (MF59/DOTAP) is an effective delivery system for DNA vaccines", Journal of Controlled Release, 2002, pp. 1-5, vol. 79.
Sznitowska et al., "Physicochemical screening of antimicrobial agents as potential preservatives for submicron emulsions", Eur. J. Pharm. Sci., Jun. 2002, pp. 489-495, vol. 15, No. 5, abstract.
Tamilvanan et al., "The potential of lipid emulsion for ocular delivery of lipophilic drugs", European Journal of Pharmaceutics and Biopharmaceutics, 2004, pp. 357-368, vol. 58.
Tamilvanan et al., "Ocular delivery of cyclosporin A—I. Design and characterization of cyclosporin A-loaded positively-charged submicron emulsion", S.T.P. Pharma Sciences, 2001, pp. 421-426, vol. 11, No. 6.
Varveri et al., "Chemiluminescence monitoring of hemolysis by lysophospholipids", Journal of Photochemistry and Photobiology A: Chemistry, 1995, pp. 121-124, vol. 91.
Washington, C., "Stability of lipid emulsions for drug delivery", Advanced Drug Delivery Reviews, 1996, pp. 131-145, vol. 20.
Xu et al., "FP Prostanoid Receptor-Mediated Induction of the Expression of Early Growth Response Factor-1 by Activation of a Ras/Raf/Mitogen-Activated Protein Kinase Signaling Cascade", http://molpharm.aspetjournals.org/content/73/1/111.long, Feb. 15, 2011, pp. 1-16.
Zuidam et al., "Chemical hydrolysis of phospholipids", J Pharm Sci., 1995, pp. 1113-1119, vol. 84, No. 9, abstract.
European Search Report, dated Oct. 29, 2010, from corresponding EP application No. EP10164376.
International Search Report, dated Aug. 20, 2010, from corresponding PCT application No. PCT/EP2010/052741.
International Search Report, dated Jul. 3, 2007, from corresponding PCT application No. PCT/EP2006/009783.
Nagai et al., "Comparison of corneal wound healing rates after instillation of commercially available latanoprost and travoprost in rat debrided corneal epithelium", Journal of Oleo Science, 2010, vol. 59, No. 3, pp. 135-141.
Wilde et al., "Interfaces: their role in foam and emulsion behaviour", Current Opinion in Colloid & Interface Sciences, 2000, vol. 5, No. 3-4, pp. 176-181.

* cited by examiner

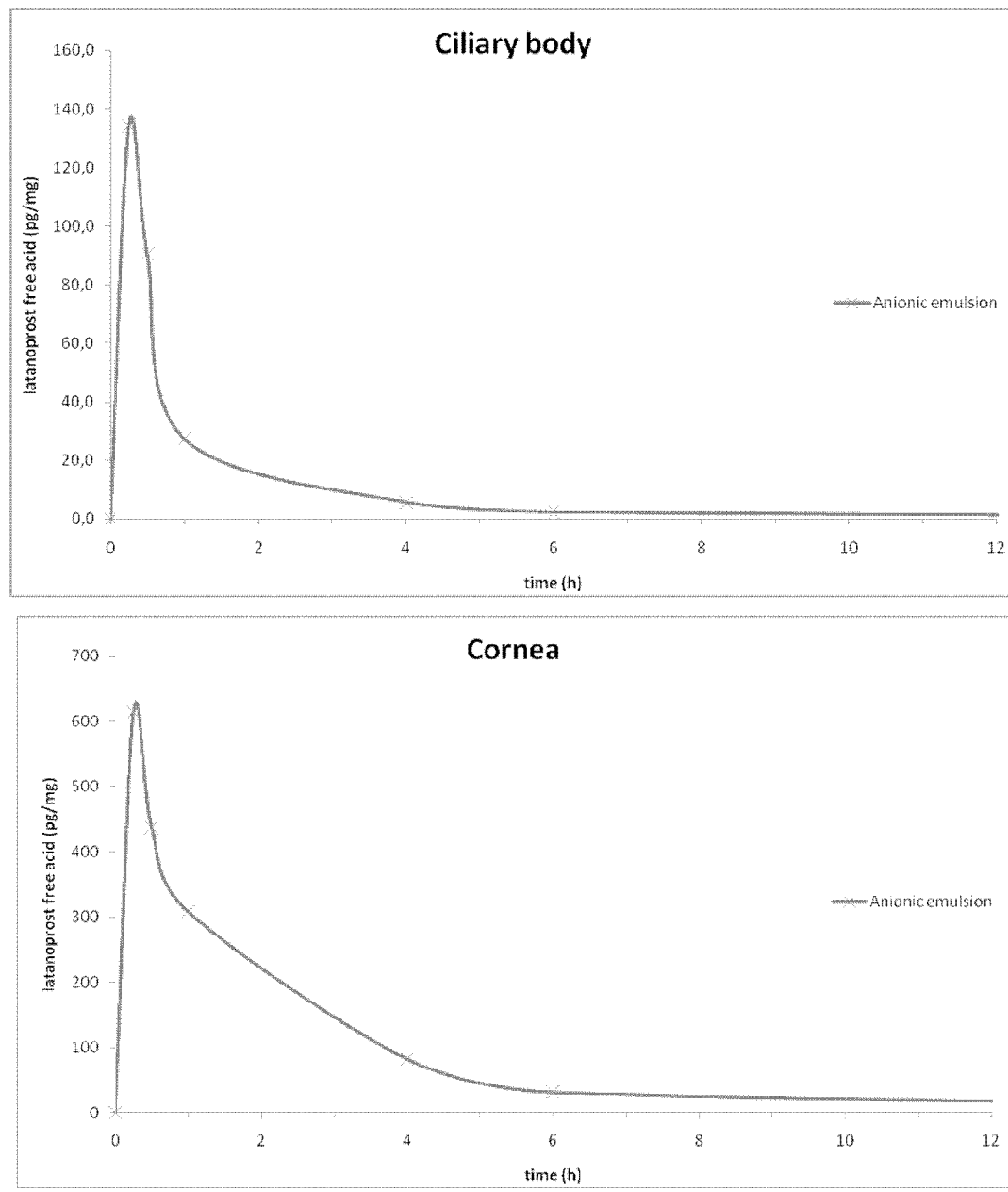

ANIONIC OIL-IN-WATER EMULSIONS CONTAINING PROSTAGLANDINS AND USES THEREOF

FIELD OF THE INVENTION

The present invention pertains to anionic oil-in-water emulsions containing prostaglandins for the topical administration of prostaglandins and in particular for the treatment of ophthalmic conditions or diseases, preferably ophthalmic conditions affecting the interior of the eye, more specifically the anterior segment of the eye, including ocular hypertension and/or glaucoma, and also for promoting growth of eyelashes and/or for treating eyelash hypotrichosis. The anionic oil-in-water emulsion according to the invention further presents the advantage to enhance the chemical stability of prostaglandins.

BACKGROUND OF THE INVENTION

Glaucoma is a disease characterized by an increase in the intraocular pressure (IOP) often associated with optic nerve damage and visual field defect. If left untreated, glaucoma can ultimately lead to blindness.

Prostaglandins, such as prostaglandin $F_{2alpha}$ and its phenyl-substituted analogues, have been shown to effectively reduce the IOP in man and animals. In fact, they have been used in ophthalmic preparations in order to treat glaucoma. For instance, latanoprost is available in the form of a topical eye solution (eyedrops) and sold under the trademark Xalatan®.

Indeed, latanoprost is a potent prostaglandin $F_{2alpha}$ analogue which has been developed for the treatment of glaucoma. Its chemical name is isopropyl—(Z)-7-[(1R,2R,3R,5S)-3,5-dihydroxy-2-[(3R)-3-hydroxy-5-phenylpentyl]-cyclopentyl]-5-heptenoate, its molecular formula is $C_{26}H_{40}O_5$ and its chemical structure is:

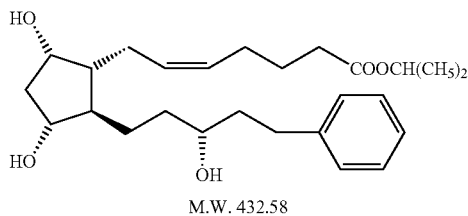

M.W. 432.58

Specifically, latanoprost is a lipophilic prodrug in which the carboxylic acid moiety in the α-chain has been esterified to increase the bioavailability of the active drug into the eye. In addition, latanoprost is absorbed through the cornea where the isopropyl ester prodrug is hydrolyzed to the acid form to become biologically active.

Some ophthalmic prostaglandins, such as bimatoprost, latanoprost or travoprost, have also been described as being capable of promoting eyelash growth. Such prostaglandins could therefore be used for the topical treatment of eyelash hypotrichosis.

The problem generally encountered with prostaglandins is that they may be chemically unstable. In particular, latanoprost is known to be very sensitive towards light and heat. Indeed, these two elements (i.e. light and heat) may have an impact on the stability of latanoprost by provoking its hydrolyzation and/or oxidation. Consequently, unopened bottles of Xalatan® should be stored in the dark and under refrigeration at 2-8° C.

Consequently, there is a need for prostaglandin formulations which show an enhanced chemical stability of the prostaglandin and, in particular, an enhanced stability overtime towards light and heat.

The Applicant already conceived prostaglandin emulsions, and found that emulsions were a suitable vehicle to stabilize prostaglandins (see for example WO2007/042262).

However, the Applicant realized that cationic emulsions containing cationic agent, preferably quaternary ammonium halides could be unsuitable to patients having an intolerance to this ingredient. This intolerance to quaternary ammoniums is related to corneal and conjunctival lesions. These lesions may be due to dry eye syndrome, allergy, injury, cataract surgery, refractive surgery with LASIK, chemical burn, traumatism, irritation, bacterial, fungal or viral infection or side effects of some medication. A corneal or conjunctival lesion is a local destruction of corneal, conjunctival or goblet cells. Such lesions may be local or disseminated and result in corneal erosion, punctuate keratopathy, epithelial defects, corneal ulceration, corneal scarring, corneal thinning, corneal perforation, keratitis, conjunctivitis, wounds, tiny abrasions, etc. These lesions are harmful and very painful. Symptoms of these lesions may be dryness, burning and a sandy-gritty eye irritation. Symptoms may also be described as itchy, scratchy, stingy or tired eyes. Other symptoms are ocular pain, redness, a pulling sensation, and pressure behind the eye. The damage to the eye surface increases discomfort and sensitivity to bright light. The Applicant thus sought for emulsions free of cationic ingredients. Whereas the Applicant thought that cationic ingredients could play a role in stabilizing prostaglandin, it is showed in this invention that, surprisingly, an emulsion containing prostaglandin and free of cationic agent is stable overtime. The Applicant excluded cationic surfactants, and directed the search to non-ionic surfactant. Surprisingly again, the use of non-ionic surfactants leads to anionic emulsions. Without being linked to any theory, the Applicant thinks that during the manufacturing process, the emulsion released negatively charged ingredients.

This invention thus relates to an anionic emulsion made of starting components which are not negatively charged. According to an embodiment of the invention, the starting materials for the manufacturing of the invention do not include any anionic surfactants.

The present invention provides a prostaglandin composition, preferably free of cationic ingredients, which exhibits an improved stability of the prostaglandin compared to commercial products, while at the same time being non toxic, tolerable for the patient with eye surface lesions and at least as efficient as the commercially available products.

OBJECTS AND DETAILED DESCRIPTION OF THE INVENTION

An object of the present invention is a colloidal oil-in-water emulsion characterized in that it comprises:
- a prostaglandin $F_{2alpha}$
- an oil having a iodine value ≤2,
- a non-ionic surfactant, and
- water,
- wherein the non-ionic surfactant releases negative charges during the manufacturing process,
- said emulsion having a negative zeta potential lower than 10 mV, and said emulsion not containing polyvinyl alcohol. According to an embodiment, the emulsion does not comprise any phospholipids. According to another embodiment, the emulsion does not comprise polyethoxylated castor oil derivatives.

According to the invention, "colloidal" means that the emulsion comprises colloid particles having an oily core surrounded by an interfacial film dispersed in water with a particle size ≤1 μm. Typically, the oily core comprises a prostaglandin and an oil. The prostaglandin being lipophilic, it is thus understandable that it is essentially present in the oily core. Typically, the emulsion may contain other ingredients, such as emollients, preferably glycerol, or pH adjusters, such as NaOH, osmotic agents and preservatives.

In the emulsion of the invention, the colloidal particles have an average particle size of equal or less than 1 μm, advantageously equal or less than 300 nm, more advantageously in the range of 100 to 250 nm.

In one embodiment, the prostaglandin is a prostaglandin $F_{2alpha}$, a derivative, precursor, prodrug or analogue thereof. Preferably, the emulsion comprises an ester prodrug, an amide prodrug of a prostaglandin $F_{2alpha}$, or a mixture thereof. Ester prodrugs include $C_1$-$C_4$ alkyl ester prodrugs, such as methyl ester, ethyl ester, isopropyl ester or butyl ester and amide prodrugs include $C_1$-$C_4$ alkyl amide prodrugs, such as methyl amide, ethyl amide, isopropyl amide or butyl amide.

According to a particular embodiment, the prostaglandin $F_{2alpha}$ of the present invention is chosen among latanoprost, isopropyl unoprostone, travoprost, bimatoprost, tafluprost, or mixtures thereof; an ester or an amide prodrug of latanoprost, isopropyl unoprostone, travoprost, bimatoprost, tafluprost; or mixtures thereof. Preferably, the emulsion according to the present invention comprises latanoprost.

The amount of prostaglandin present in the oily core of the emulsion according to the invention depends on the nature of the prostaglandin $F_{2alpha}$ and to the intended use. In a preferred embodiment of the invention, the amount of prostaglandin $F_{2alpha}$ relative to the total weight of the emulsion is comprised between 0.001 to 1% w/w, preferably between 0.002 to 0.3% w/w and even more preferably between 0.004 to 0.15% w/w.

In a particular embodiment, the prostaglandin may be combined with other anti-glaucoma active ingredients, such as for example dorzolamide or timolol.

In another embodiment, the emulsion is an ophthalmic emulsion, comprising an effective amount of prostaglandin $F_{2alpha}$, for use in the treatment of ocular hypertension and/or glaucoma.

According to the present invention, the oil is preferably chosen among saturated oils.

According to the invention, a "saturated oil" is an oil which has an iodine value of less or equal to 2, preferably less than 2, which means that the oil is substantially free of any molecule having a hydrocarbon chain containing double or triple bonds.

The iodine value can be measured for example, according to methods disclosed in the European Pharmacopeia monograph 2.5.4 or US Pharmacopeia 401.

According to a particular embodiment of the present invention, the oil is chosen among oily fatty acids, oily fatty alcohols, fatty acids esters such as isopropyl myristate, isopropyl palmitate, vegetable oils, animal oils, mineral oils such as petrolatum, liquid paraffin, semi-synthetic oils such as fractionated oils obtained from vegetable oils or mixtures thereof.

According to the invention "semi-synthetic oils" are prepared by chemical synthesis from natural oils.

Particularly, the oil according to the invention is a semi-synthetic oil obtained from fractionated coconut oil, kernel oil or babassu oil. More particularly, the oil is medium chain triglycerides (MCT).

Indeed, according to the European Pharmacopeia, medium-chain triglycerides (MCT) is described as the fixed oil extracted from the hard, dried fraction of the endosperm of *Cocos nucifera* L. by hydrolysis, fractionation of the fatty acids obtained, and re-esterification. MCT consists of a mixture of exclusively short- or medium-chain triglycerides of fatty acids, of which not less than 95% are the saturated fatty acids octanoic (caprylic) acid and decanoic (capric) acid.

Moreover, MCT can also be found in substantial amounts in kernel oil and babassu oil, in addition to some animal products, such as milk-fat, which may contain small amounts (up to 4%) of MCT.

In another embodiment of the invention, the pH of the emulsion is preferably comprised between 4 and 7, particularly between 4.5 and 6.5 and more particularly between 5 and 6.

In a preferred embodiment of the invention, the amount of the oil relative to the total weight of the emulsion is not higher than 7% w/w, preferably between 0.5 and 5% w/w and even more preferably between 1 and 3% w/w.

Typically, the nonionic surfactants which may be present in the emulsion of the invention comprise alkyl polyethylene oxide, alkylphenol polyethylene oxide, poloxamers, tyloxapol, alkyl polyglucosides, fatty alcohols, cocamide MEA, cocamide DEA, sorbitan esters, polyoxyl stearates, polysorbates or mixtures thereof.

In a preferred embodiment of the invention, the emulsion contains polysorbates, preferably polysorbate 80. According to an embodiment of the invention, the emulsion contains only one non-ionic surfactant, which preferably is polysorbate 80. In another embodiment, the emulsion comprises an effective amount of prostaglandin $F_{alpha}$, polysorbate 80, MCT, glycerol and water.

In another embodiment of the invention, the emulsion may also comprise anionic surfactants such as perfluorooctanoate, perfluorooctanesulfonate, alkyl sulphate salts, sodium lauryl ether sulphate, alkyl benzene sulfonate, soaps or fatty acid salts or mixtures thereof.

Typically, the zwitterionic surfactants comprise dodécyl betaine, cocamidopropyl betaine, coco ampho glycinate or mixtures thereof.

Typically, the surfactant according to the invention comprises hydrophilic surfactants (with a high HLB) and/or hydrophobic surfactant (with a low HLB) or mixtures thereof.

In a particular embodiment, the surfactants are chosen among poloxamers, tyloxapol, polysorbates, sorbitan esters, polyoxyl stearates or mixtures thereof.

In another embodiment, the emulsion is free of any cationic agent, especially cationic surfactant.

In another embodiment, the emulsion is free of water soluble polymers, especially free of water soluble polymers chosen among polyvinyl compounds, water-soluble cellulose compounds or polysaccharides.

In particular embodiments, the prostaglandin $F_{2alpha}$/total sum of surfactants mass ratio in the emulsion is comprised between 0.01 and 5, or between 0.01 and 4, or between 0.01 and 3, or between 0.01 and 2, or between 0.01 and 1, or between 0.01 and 0.99, or between 0.02 and 0.08, or between 0.04 and 0.06 or is around 0.05.

In one embodiment, the amount of the surfactant relative to the total weight of the emulsion is comprised between 0.0005 and 1% w/w, preferably between 0.001 and 0.5% w/w and even more preferably between 0.01 and 0.5% w/w; provided that the prostaglandin $F_{2alpha}$/total sum of surfactants mass ratio in the emulsion is comprised between 0.01 and 5.

The emulsion according to the invention has a negative zeta potential. This negative zeta potential is preferably lower than −10 mV (−10 mV excluded), preferably lower than −15 mV more preferably lower or equal to −20 mV.

It has long been recognised that the zeta potential is a very good index of the magnitude of the interaction between colloidal particles and measurements of zeta potential are commonly used to assess the stability of colloidal systems. The zeta potential measured in a particular system is dependent on the chemistry of the surface, and also of the way it interacts with its surrounding environment.

Typically, the emulsions according to the invention are physically stable overtime and keep a negative zeta potential over a period of two years at 25° C. The zeta potential of the emulsion droplet surface is determined by electrophoretic mobility in an apparatus such as a Malvern Zetasizer 2000 (Malvern Instruments, UK) equipped with suitable software and calibrated with the supplied standard.

The emulsion is diluted in double distilled water if needed in order to obtain the scattering intensity allowing optimal particle detection. The sample count rate should be between 100 to 1000 KCps, in homodyne detection (if heterodyne detection is used, the contribution of the reference beam should be deduced). Three consecutive measurements are performed at 25° C. using a constant cell drive of 150 mV. The electrophoretic mobility is converted into zeta potential values through the Smoluchowsky equation, using the dielectric constants and viscosity of water. The measured value corresponds to the average of the 3 obtained values.

In a particular embodiment, the emulsion of the invention is free of any buffer.

According to the invention, the emulsion remains physically stable during autoclaving. According to the present invention, "autoclaving" is defined as sterilization of a product by steam under pressure, by heating said product in an autoclave at high temperatures (e.g. 100 to 200° C., preferably 121° C.) during an extended period of time (e.g. 10 to 60 minutes, preferably 10 to 20 minutes) at around 103 kPa (15 psi) above atmospheric pressure. The steam and pressure transfer sufficient heat into organisms to kill them and thus sterilize the product.

According to the invention, "stability" is defined as the extent to which a product retains, within specified limits and throughout its period of storage and use (i.e., its shelf life), the same properties and characteristics that it possessed at the time of manufacture.

The purpose of stability testing is to provide evidence concerning the quality of a drug substance or a drug product overtime, said product being subjected to a variety of environmental factors such as temperature, humidity and light. The result may be helpful in providing appropriate storage conditions, re-testing periods and shelf lives.

Although conventional stability studies do evaluate those factors which ultimately affect the expiration date of the drugs, these conventional studies are time and cost-consuming. Consequently, in order to predict shelf life of a pharmaceutical product for example, the pharmaceutical industry usually uses "accelerated stability studies" (Stress Test). These accelerated studies help understand the intrinsic stability mechanism of the molecule of interest by establishing degradation pathways and by identifying the likely degradation products. In these types of studies, the products are usually subjected to extreme conditions, such as temperature of about 40° C. for approximately 6 months.

In the present invention, the Applicant has developed a "Stress Test" during which the emulsions are subjected to a temperature of 80° C. for 14 days.

According to the invention, "good tolerability" means that the ratio "therapeutic benefit" to "ocular discomfort" is acceptable by the patient, and preferably similar to a placebo or NaCl solution 0.9%.

Another object of the present invention is a process for manufacturing the emulsion previously described. Especially, this invention relates to the manufacture of an emulsion having a negative zeta potential, from starting materials which do not contain anionic surfactants, but contain non-ionic surfactants showing the ability to release negative ingredients during the manufacturing process.

The process of the invention uses as starting materials,
   a prostaglandin $F_{2alpha}$
   an oil having a iodine value ≤2,
   a non-ionic surfactant, and
   water said process comprising preparing an oily phase by mixing the prostaglandin with the oil, preparing an aqueous phase by mixing the non-ionic surfactant and the water; shear mixing the oily phase and the aqueous phase, adjusting the pH of the resulting emulsion, and optionally autoclaving the resulting emulsion.

According to a preferred embodiment, the process of the invention includes the following steps:
   preparation of the oily phase by mixing the prostaglandin (such as for example latanoprost) with the saturated oil (such as for example MCT);
   preparation of the aqueous phase by mixing the water-soluble ingredients (such as for example glycerol and/or polysorbate 80) with purified water;
   incorporating the oily phase to the aqueous phase;
   rapidly heating the coarse emulsion obtained, preferably at 75° C.;
   decreasing the emulsion droplet size by any suitable means known to the man skilled in the art, for example by shear mixing;
   cooling down the emulsion preferably to about 20° C. using an ice bath;
   homogenizing the cooled emulsion;
   optionally, adjusting the pH to a physiological pH, for example by using NaOH or HCl;
   preferably sterilizing, more preferably sterilizing by autoclaving.

The emulsion according to the present invention is preferably intended to be applied topically, to the surface of the eye or to hairs, such as eyelashes.

An object of the present invention is the anionic oil-in-water emulsion according to the invention for use in a method for treating ocular hypertension and/or for treating glaucoma.

An object of the present invention is the anionic oil-in-water emulsion according to the invention for use in a method for promoting growth of eyelashes or treating eyelash hypotrichosis.

An object of the present invention is an ophthalmic formulation comprising the anionic oil-in-water emulsion according to the invention, optionally in combination with an ophthalmologicallly acceptable carrier. It may be in the form of eye drops, eye ointment, or ophthalmic gel.

An object of the present invention is the use of the anionic oil-in-water emulsion according to the invention in order to enhance the chemical stability of prostaglandins.

An object of the present invention is a delivery device comprising the anionic oil-in-water emulsion according to the invention.

Typically the delivery device according to the invention is selected from the group comprising lenses, ocular patch, implant, insert.

Other features and advantages of the invention will emerge upon reading the following non limiting examples.

BRIEF DESCRIPTION OF THE FIGURES

FIG. 1: Latanoprost free acid concentration in ciliary body and in cornea after administration of the emulsion of the invention.

EXAMPLES

1. Preparation of an Anionic Oil-in-water Emulsion.

The anionic oil-in-water emulsion according to the present invention is prepared by the following steps:

- preparation of the oily phase by mixing at 50° C. the prostaglandin (latanoprost) with the saturated oil (MCT);
- preparation of the aqueous phase by mixing at 50° C. glycerol, polysorbate 80 and purified water;
- incorporating the oily phase to the aqueous phase;
- rapidly heating the coarse emulsion obtained at 75° C.;
- decreasing the emulsion droplet size by any suitable means known to the man skilled in the art, for example by shear mixing 5 minutes at 16000 rpm (Polytron PT6100, Kinematica, Switzerland);
- cooling down the emulsion to about 20° C. using an ice bath;
- homogenizing during 20 minutes at 15000 psi the cooled emulsion (Emulsiflex C3, Avestin, Canada);
- pH is adjusted with NaOH 1M at pH 7;
- sterilizing the emulsion by autoclaving.

The composition of the emulsion is given in table 1.

TABLE 1

|  | Ingredients | Theorethical composition (% w/w) |
|---|---|---|
| Oily phase | MCT (Sasol GmBH, Germany) | 1.000 |
|  | Latanoprost | 0.005 |
| Aqueous phase | Glycerol (Merck, Germany) | 2.400 |
|  | Polysorbate 80 (Seppic, France) | 0.100 |
|  | Water (up to 100) | 96.495 |
|  | NaOH 1M | qs pH 7 |
|  | Total | 100% |

MCT (Medium Chain Triglycerides)
qs: quantum satis

2. Stability Test & Comparative Test

The stability of the emulsion of example 1 was evaluated under accelerated conditions "Stress Test" (at 80° C. during 14 days), while a comparative analysis was conducted between the anionic emulsion (invention) and Xalatan® under the same "Stress Test" conditions. Prostaglandin content was analysed in both tests by an HPLC-UV method.

The results are given in table 2 (stability test) and Table 3 (comparative test).

TABLE 2

| Emulsion of ex. 1 | Aspect | Zeta potential (mV) | Osmolality (mOsm/kg) | pH | Droplet size (nm) | Latanoprost (% w/w) |
|---|---|---|---|---|---|---|
| T = 0 Days | White milky homogeneous emulsion (Tyndall effect) | −22.2 | 279 | 6.99 | 167 | 0.00514 |
| T = 14 Days | White milky homogeneous emulsion (Tyndall effect) | −33.7 | 288 | 5.61 | 186 | 0.00528 |

The emulsions according to the present invention show a remarkable stability after being subjected to such stress testing conditions (i.e. Stress Test) during at least 14 days.

TABLE 3

|  | Latanoprost (% w/w) | | pH | | Zeta Potential (mV) | |
|---|---|---|---|---|---|---|
|  | T0 (days) | T14 (days) | T0 (days) | T14 (days) | T0 (days) | T14 (days) |
| Emulsion of ex. 1 | 0.00514 | 0.00528 | 6.99 | 5.61 | −22.2 | −33.7 |
| Xalatan ® | 0.00510 | 0.00248 | 6.74 | 6.71 | NA | NA |

At T0, the concentrations in prostaglandins for the emulsion (invention) and for Xalatan® are close to 0.005%. However, after subjecting both emulsions to the "Stress Test" (14 days at 80° C.), it can be observed that the concentration of prostaglandins remains the same for the emulsion (invention), while it has decreased by more than half in the case of Xalatan®.

3. Pharmacokinetic/Pharmacodynamic Studies of the Emulsion of Table 1

Male and female New Zealand White rabbits were administrated with the emulsion of Table 1 and latanoprost free acid concentration was determined at different time points after administration (0.25, 0.5, 1, 4, 6 and 24 hour(s)) at the following target tissues: conjunctiva, cornea, aqueous humor and ciliary body. Tmax and AUC 0.5-24 h were calculated and are presented hereafter in Table 4. The latanoprost free acid is the latanoprost which was hydrolized by esterase into its active form.

TABLE 4

| | Numerical field name | Units | Anionic emulsion |
|---|---|---|---|
| Aqueous humor | $T_{max}$ | h | 0.25-0.5 |
| | $AUC_{0.25-24\,h}$ | pg × h/μl | 153 |
| Cornea | $T_{max}$ | h | 0-0.25 |
| | $AUC_{0.25-24\,h}$ | pg × h/mg | 1033 |
| Conjunctiva | $T_{max}$ | h | 0-0.25 |
| | $AUC_{0.25-24\,h}$ | pg × h/mg | 144 |
| Ciliary body | $T_{max}$ | h | 0-0.25 |
| | $AUC_{0.25-24\,h}$ | pg × h/mg | 112 |

Tmax represents the time at which the maximal concentration of latanoprost free acid is reached FIG. 1 (ciliary body and cornea) and results here above presented show that latanoprost free acid is present at a high concentration in the target ocular tissues after administration of the emulsion. Said concentrations are known to be sufficient to allow the opening of the Schlemm's canal and thus evacuation of aqueous humor, thereby reducing the intraocular pressure.

The invention claimed is:

1. A colloidal oil-in-water emulsion comprising
    a prostaglandin $F_{2alpha}$
    an oil having a iodine value ≤2,
    a non-ionic surfactant selected from the group consisting of poloxamers, tyloxapol, polysorbates, sorbitan esters, polyoxyl stearates and mixtures thereof, and
    water,
wherein the non-ionic surfactant, the amount of which is comprised between 0.0005 and 1% in weight by weight of said emulsion, releases negative charges during the manufacturing process of the emulsion, said emulsion having a negative zeta potential lower than −10 mV, said emulsion not containing polyvinyl alcohol, and said emulsion being free of cationic surfactant.

2. The colloidal oil-in-water emulsion according to claim 1, wherein the prostaglandin $F_{2alpha}$ is selected from the group consisting of latanoprost, isopropyl unoprostone, travoprost, bimatoprost, tafluprost ; an ester or an amide prodrug of latanoprost, isopropyl unoprostone, travoprost, bimatoprost, tafluprost ; and mixtures thereof.

3. The colloidal oil-in-water emulsion according to claim 1, wherein the oil is selected from the group consisting of oily fatty acids, oily fatty alcohols, fatty acids esters, vegetable oils, animal oils, mineral oils, liquid paraffin, semi-synthetic oils and mixtures thereof.

4. The colloidal oil-in-water emulsion according to claim 3, wherein the oil is medium chain triglycerides (MCT).

5. The colloidal oil-in-water emulsion according to claim 1, wherein the amount of prostaglandin $F_{2alpha}$ relative to the total weight of the emulsion is comprised between 0.001 to 1% w/w.

6. The colloidal oil-in-water emulsion according to claim 1, wherein the amount of the oil relative to the total weight of the emulsion is not higher than 7% w/w.

7. The colloidal oil-in-water emulsion according to claim 1, wherein the emulsion is free of any buffer.

8. A method for treating ocular hypertension and/or glaucoma comprising administering to a subject in need thereof a colloidal oil-in-water emulsion comprising
    a prostaglandin $F_{2alpha}$
    an oil having a iodine value ≤2,
    a non-ionic surfactant selected from the group consisting of poloxamers, tyloxapol, polysorbates, sorbitan esters, polyoxyl stearates and mixtures thereof, and
    water,
wherein the non-ionic surfactant, the amount of which is comprised between 0.0005 and 1% in weight by weight of said emulsion, releases negative charges during the manufacturing process of the emulsion, said emulsion having a negative zeta potential lower than −10 mV, said emulsion not containing polyvinyl alcohol, and said emulsion being free of cationic surfactant.

9. The method according to claim 8, wherein the prostaglandin $F_{2alpha}$ is selected from the group consisting of latanoprost, isopropyl unoprostone, travoprost, bimatoprost, tafluprost ; an ester or an amide prodrug of latanoprost, isopropyl unoprostone, travoprost, bimatoprost, tafluprost ; and mixtures thereof.

10. The method according to claim 8, wherein the oil is selected from the group consisting of oily fatty acids, oily fatty alcohols, fatty acids esters, vegetable oils, animal oils, mineral oils, liquid paraffin, semi-synthetic oils and mixtures thereof.

11. The method according to claim 10, wherein the oil is medium chain triglycerides (MCT).

12. A delivery device comprising a colloidal oil-in-water emulsion comprising
    a prostaglandin $F_{2alpha}$
    an oil having a iodine value ≤2,
    a non-ionic surfactant selected from the group consisting of poloxamers, tyloxapol, polysorbates, sorbitan esters, polyoxyl stearates and mixtures thereof, and
    water,
wherein the non-ionic surfactant, the amount of which is comprised between 0.0005 and 1% in weight by weight of said emulsion, releases negative charges during the manufacturing process of the emulsion, said emulsion having a negative zeta potential lower than −10 mV, said emulsion not containing polyvinyl alcohol, and said emulsion being free of cationic agent.

13. The delivery device according to claim 12, wherein the prostaglandin prostaglandin $F_{2alpha}$ is selected from the group consisting of latanoprost, isopropyl unoprostone, travoprost, bimatoprost, tafluprost ; an ester or an amide prodrug of latanoprost, isopropyl unoprostone, travoprost, bimatoprost, tafluprost ; and mixtures thereof.

14. The colloidal oil-in-water emulsion according to claim 1, wherein the amount of the surfactant relative to the total weight of the emulsion is between 0.001 and 0.5% w/w.

15. The colloidal oil-in-water emulsion according to claim 14, wherein the amount of the surfactant relative to the total weight of the emulsion is between 0.01 and 0.5% w/w.

* * * * *